(12) United States Patent
Meixner et al.

(10) Patent No.: US 8,220,242 B2
(45) Date of Patent: *Jul. 17, 2012

(54) CHARACTERIZATION OF FANCY YARN

(75) Inventors: Christine Meixner, Wald (CH);
Gabriela Peters, Fehraltorf (CH);
Sandra Edalat-Pour, Hadlikon (CH)

(73) Assignee: Uster Technologies, AG, Uster (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/906,342

(22) Filed: Oct. 18, 2010

(65) Prior Publication Data

US 2011/0061359 A1  Mar. 17, 2011

Related U.S. Application Data

(63) Continuation of application No. 12/093,495, filed as application No. PCT/CH2006/000642 on Nov. 15, 2006, now Pat. No. 7,836,674.

(30) Foreign Application Priority Data

| Nov. 18, 2005 | (CH) | 1846/05 |
| Dec. 23, 2005 | (CH) | 2059/05 |
| Jun. 8, 2006 | (CH) | 925/06 |
| Jun. 21, 2006 | (CH) | 1004/06 |

(51) Int. Cl.
*D01H 13/32* (2006.01)
(52) U.S. Cl. .......................... 57/264; 57/265
(58) Field of Classification Search .............. 57/264, 57/265; 700/139, 144
See application file for complete search history.

(56) References Cited

U.S. PATENT DOCUMENTS

| 4,491,831 | A | 1/1985 | Sakai et al. |
| 4,924,406 | A | 5/1990 | Bergamini et al. |
| 5,119,308 | A | 6/1992 | Samoto |
| 5,146,550 | A | 9/1992 | Furter et al. |
| 5,537,811 | A | 7/1996 | Pidoux et al. |
| 5,748,481 | A | 5/1998 | Nakade |
| 5,875,419 | A | 2/1999 | Nevel et al. |
| 7,626,189 | B2 | 12/2009 | Meixner et al. |
| 7,832,190 | B2 * | 11/2010 | Meixner et al. ............... 57/265 |
| 7,836,674 | B2 * | 11/2010 | Meixner et al. ............... 57/265 |
| 2003/0107729 | A1 | 6/2003 | Furter |
| 2007/0022728 | A1 | 2/2007 | Biermann |
| 2007/0277495 | A1 | 12/2007 | Biermann et al. |
| 2008/0288101 | A1 | 11/2008 | Meixner et al. |

* cited by examiner

*Primary Examiner* — Shaun R Hurley
(74) *Attorney, Agent, or Firm* — Luedeka Neely Group, P.C.

(57) ABSTRACT

According to the method for characterizing fancy yarn, at least one characteristic of the fancy yarn is scanned along the longitudinal direction of the fancy yarn. Values of the scanning are evaluated and the results of the evaluation are outputted. The results of the evaluation are the fancy yarn parameters such as base yarn mass, base yarn diameter, stub distance, mass increase ($\Delta M$) of a stub, slub diameter increase, stub diameter, slub length ($L_E$) and/or slub total mass. At least one result of the evaluation is outputted in the form of a graphic representation, for example as a scatter diagram. Such a graphic representation provides a clear representation of the measurement results. The occurring data is reduced and may be divided up into different categories.

17 Claims, 15 Drawing Sheets

|  |  |  | 69 | 21 |  |
|---|---|---|---|---|---|
|  |  |  | 98 | 10 |  |
|  |  |  |  | 7 | 15 |
|  | 93 | 46 |  | 58 | 22 |
|  |  | 2 |  |  |  |

ΔM (vertical axis), $L_E$ (horizontal axis)

Fig. 7

|  | $L_E$ | | | $L_S$ | | | ΔM | | | Δ Diameter | | | # |
|---|---|---|---|---|---|---|---|---|---|---|---|---|---|
|  | Min | ⌀ | Max | Min | ⌀ | Max | Min | ⌀ | Max | Min | ⌀ | Max |  |
| Total |  |  |  |  |  |  |  |  |  |  |  |  |  |
| Popul. 111 |  |  |  |  |  |  |  |  |  |  |  |  |  |
| Popul. 112 |  |  |  |  |  |  |  |  |  |  |  |  |  |
| Popul. 113 |  |  |  |  |  |  |  |  |  |  |  |  |  |

Fig. 8

CHARACTERIZATION OF FANCY YARN

This application claims all rights and priority on prior U.S. patent application Ser. No. 12/093,495 filed 2008 May 13, now U.S. Pat. No. 7,836,674 issued 2010 Nov. 23. The invention relates to a method for the characterization of fancy yarn. It may be applied in the textile laboratory (offline) as well as in textile production (online), e.g. in spinning works or winding works.

FIELD OF THE INVENTION

State of the Art

Fancy yarn is yarn whose structure or fiber composition differs from the normal smooth yarn. It is applied in weaving mill products and knitting mill products as an enriching element. Fancy yarn usually has a multitude of thick places or thin places—so-called slubs—whose diameter is significantly larger or smaller than the diameters of the yarn sections lying between the slubs—the so-called base yarn. Structured yarn with deliberately produced thickness variations with which no base yarn may be identified is however also counted among the fancy yarns. The increasing popularity of fancy yarn demands reliable and meaningful methods for its characterization. Variables such as base yarn diameter, diameter increase at a slub, slub mass, slub length, slub distance, etc. are of particular interest. These variables may e.g. be used for the control of the quality of the present fancy yarn or for determining the manufacturing parameters which are necessary for copying a given fancy yarn.

Methods and devices for characterization of yarn are known. They are usually based on a capacitive and/or optical scanning of the yarn moved in the longitudinal direction. The capacitive scanning principle provides a signal corresponding to the yarn mass, whilst the optical scanning principle provides a signal proportional to the yarn diameter. The scanning signal is evaluated in an analog or digital manner, and one or several results of the evaluation are outputted. Examples of such methods and devices for the characterization of yarn are specified in the patent publications EP-0'578'975 A1 or EP-0'249'741 A2. Both relate to the yarn testing system USTER®TESTER which is marketed worldwide by the proprietor of the present protective property right.

It is also known to obtain information on the color, i.e. on the spectral reflection characteristics of yarn. Thus e.g. according to WO-2004/044579, one applies a multi-colored light source for illuminating the yarn. The light reflected by the yarn is detected separately in at least two different spectral ranges. The at least two detection signals permit information with regard to the yarn color. A simultaneous optical scanning of a textile material at different wavelengths is also known from CH 674'379 or from DE-198'59'274.

WO-2005/071'150 A1, WO-2005/038'105 A1 and WO-2005/037699 A1 especially deal with fancy yarn. The teaching of the latter document may be summarized as follows:

determining the base yarn diameter: Firstly, the arithmetic mean of the yarn diameter is formed over a large yarn length. This mean is subtracted from the individual values of the yarn diameter. The arithmetic means of all negative values which have been measured adjacently to the other negative values is defined as the base yarn diameter.

determining the beginning, end and length of a slub: A slub beginning is present if a limit diameter which lies above the base yarn diameter is overshot, and the overshoot persists over a certain yarn length. A slub end is present if the limit diameter is undershot, and the undershoot persists over a certain yarn length. The slub length is defined as a distance between the slub beginning and the slub end.

determining the slub diameter. A plurality of the largest diameters is determined within a slub. The slub diameter is defined as the mean of these largest diameters.

Although this teaching permits a useful characterization of fancy yarn, it also has a few disadvantages. A large quantity of data occurs as a result, which is unclear and difficult to handle. Suitable possibilities for the clear representation of the readings are not specified. The described method, if anything, results in a base yarn diameter which is too large and in a slub length which is too small.

DESCRIPTION OF THE INVENTION

It is an object of the present invention to specify a method for the characterization of fancy yarn which provides a clear representation of the measurement results. The occurring data should be reduced compared to the teaching of WO-2005/037688 A1. Furthermore, the invention should permit the occurring data to be divided up into certain categories in a suitable manner, i.e. into data which concern the slubs, and data which concern imperfections of the yarn.

These and other objects are achieved by the methods defined in the claims.

According to the method according to the invention, for the characterization of fancy yarn which preferably has a sequence of slubs and base yarn, at least one characteristic of the fancy yarn is scanned along the longitudinal direction of the fancy yarn. Values of the scanning are evaluated and results of the evaluation are outputted. Results of the evaluation are outputted: it is preferably the case of fancy yarn parameters such as base yarn mass, base yarn diameter, slub distance, mass increase of a slub, slub diameter increase, slub diameter, slub length and/or slub mass. At least one result of the evaluation is outputted in the form of a graphic representation. Such a graphic representation reduces the occurring data quantity. It permits a rapid visual perception of the results. By way of this, it is also possible to divide up the data into different categories. In a preferred embodiment, the graphic data is a scatter diagram, and the at least one scanned characteristic is a mass and/or a diameter of the fancy yarn.

LISTING OF THE DRAWINGS

The invention is hereinafter described in more detail by way of the drawings.

FIG. 1 schematically shows a device for carrying out the method according to the invention.

FIGS. 5-15 show possible representation types according to the invention, for outputting the yarn parameters.

IMPLEMENTATION OF THE INVENTION

Figure 1:
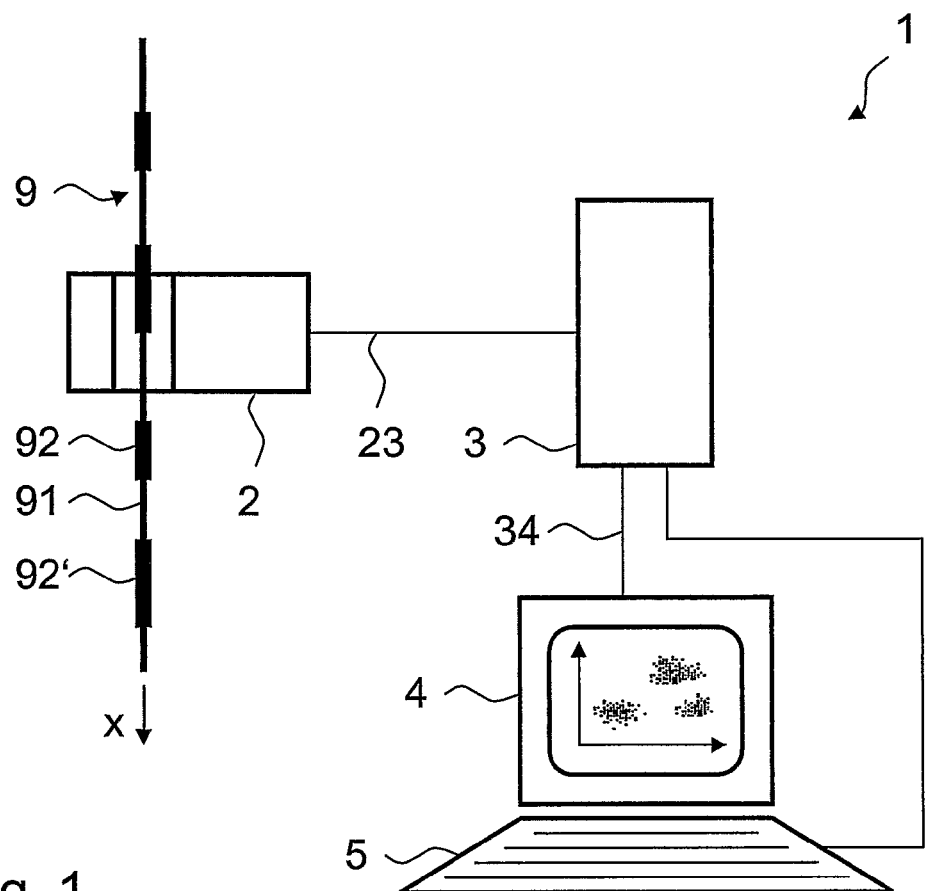

A device 1 for carrying out the method according to the invention is shown schematically in FIG. 1. It contains a scanning unit 2 for scanning a fancy yarn 9 with base yarn 91 and slubs 92, 92', which is moved in a longitudinal direction—x. Here, the sequential recording of a multitude of readings at different, preferably equidistant locations of the fancy yarn 9 is to be understood under the term "scanning". Such scanning units 2 are known per se, and do not need to be explained in more detail here. The scanning unit 2 may contain a capacitive, optical or other sensor; also several equal or different sensors may be arranged within the scanning unit 2. The scanning unit 2 may be provided with evaluation means for a preliminary evaluation of the readings. It outputs a preferably electrical output signal which is a measure for the mass, the thickness or other characteristics of the fancy yarn 9, on a first data lead 23.

The first data lead 23 runs into an evaluation unit 3 which is suitable for evaluating the output signal of the scanning unit 2. For this purpose, it contains suitable analog and/or digital evaluation means, e.g. a microprocessor. It may also contain further means such as memory means for storing data. The evaluation unit 3 is preferably a computer.

Furthermore, the device 1 contains an output unit 4 for outputting measurement data and/or results of the evaluation. The output unit 4 is connected to the evaluation unit 3 by way of a second data lead 34. It may e.g. be designed as a monitor and/or printer. The device 1 preferably also contains an input unit 5 for inputting data on the part of the user. The input unit 5 may e.g. be a keyboard, a mouse and/or a touch screen.

Figure 2:
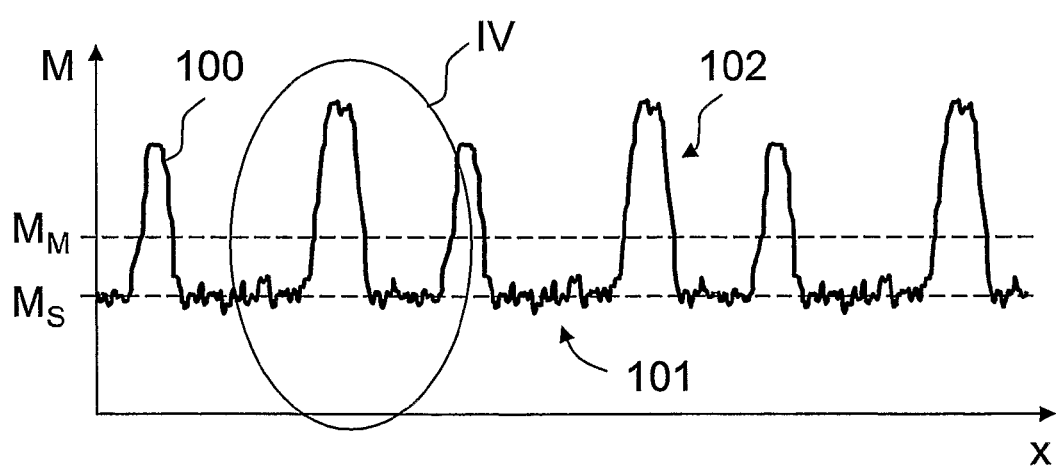
FIG. 2 shows one example of a series of readings with regard to a fancy yarn, specifically yarn mass against length coordinate.

FIG. 2 shows one possible output signal 100 of the scanning unit 2. Thereby, a variable for example which is a measure for the mass M per unit length of the fancy yarn 9 (see FIG. 1), is plotted along the length coordinate x of the fancy yarn 9. Such a measure signal M is typically provided by a capacitive yarn sensor. A representation of the thickness of the fancy yarn 9 along the length coordinate x would appear in a similar manner, wherein the scales on the abscissa and the ordinate as well as the resolution could be different; a thickness signal is typically provided by an optical yarn sensor. The curve M(x) is not necessarily continuous, but may be composed of individual (not shown in FIG. 2) scanning points which on the fancy yarn 9 are typically distanced from one another by a few millimeters; the distance depends on the scanning rate of the scanning unit 2 and on the speed of the fancy yarn 9. The signal M(x) has a noise floor 101 which corresponds to the base yarn mass $M_S$ or the base yarn diameter. The peaks 102 corresponding to the slubs project significantly from the noise floor 101. A mean $M_M$ of all readings M(x) over a large yarn length, on account of the peaks 102, lies significantly above the noise floor 101 and is therefore not suitable as a measure for the base yarn mass $M_S$. At this location, it should be noted that FIG. 2 and the subsequent discussion only represents one possible, non-limiting example. With other types of fancy yarn, it is no longer even possible to identify base yarn.

Figure 3:
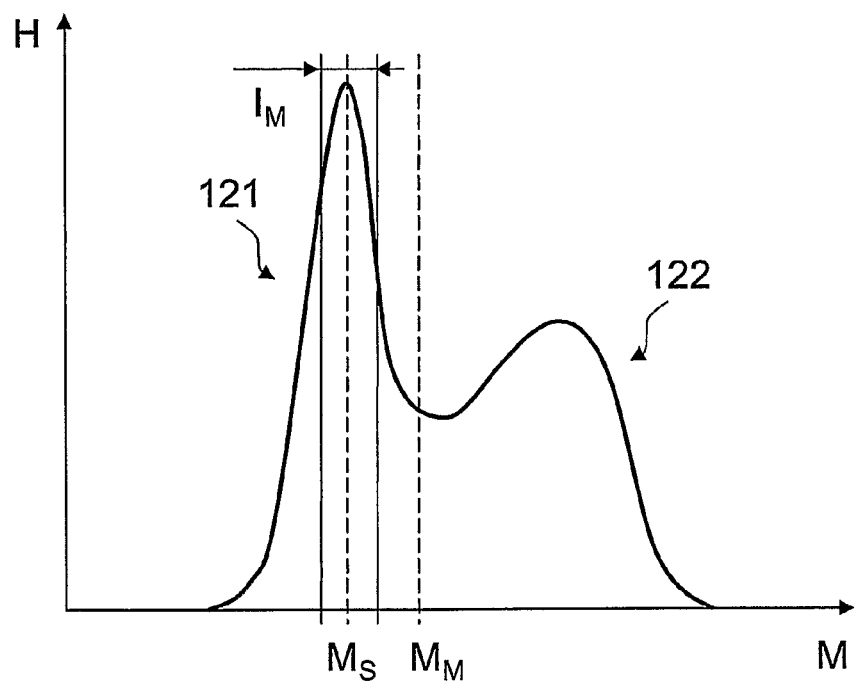
FIG. 3 shows a frequency distribution of the measured yarn mass plotted in FIG. 2.

The base yarn mass $M_S$ may be determined according to the present invention preferably as follows. A frequency distribution H(M) of the measured masses M represented in FIG. 2 is determined. Such a frequency distribution H(M) is schematically shown in FIG. 3. The frequency distribution H(M) must be determined for a large yarn length, under which here a yarn length is to be understood as one which contains may slubs, for example at least 10 and preferably at least 100. The frequency distribution H(M) with an fancy yarn 9 comprises at least two local maxima 121, 122: a first local maximum 121 for the base yarn 91, and at least one second local maximum 122 for the slubs 92, 92', .... According to definition, amongst all local maxima 121, 122, it is the local maximum 121 belonging to the base yarn 91 which has the smallest mass M. For this reason, the smallest mass M at which a local maximum 121 occurs in the frequency distribution H(M) is defined as the base yarn mass $M_S$. The yarn number of the yarn body or of the base yarn 91 may be computed from the base yarn mass $M_S$. One may proceed in an analogous manner in order to determine the base yarn diameter.

According to an alternative embodiment of the method according to the invention for determining the base yarn mss, one defines a mass interval $I_M$ (see FIG. 3) which contains that smallest mass at which a local maximum 121 occurs in the frequency distribution H(M). The mass interval $I_M$ may, but need not be symmetrical with respect to the "smallest" mass, i.e. the "smallest" mass may, but need not lie in the middle of the mass interval $I_M$. The upper limit of the mass interval $I_M$ is preferably selected below the global mass mean $M_M$. The width and the position of the mass interval $I_M$ may be predefined in a fixed manner—for example ±5% of the "smallest" mass—automatically computed by the evaluation unit 3, or be inputted by a user. A mean is subsequently formed over all masses M measured in this mass interval $I_M$. The base yarn mass is defined as this mean.

Figure 4:
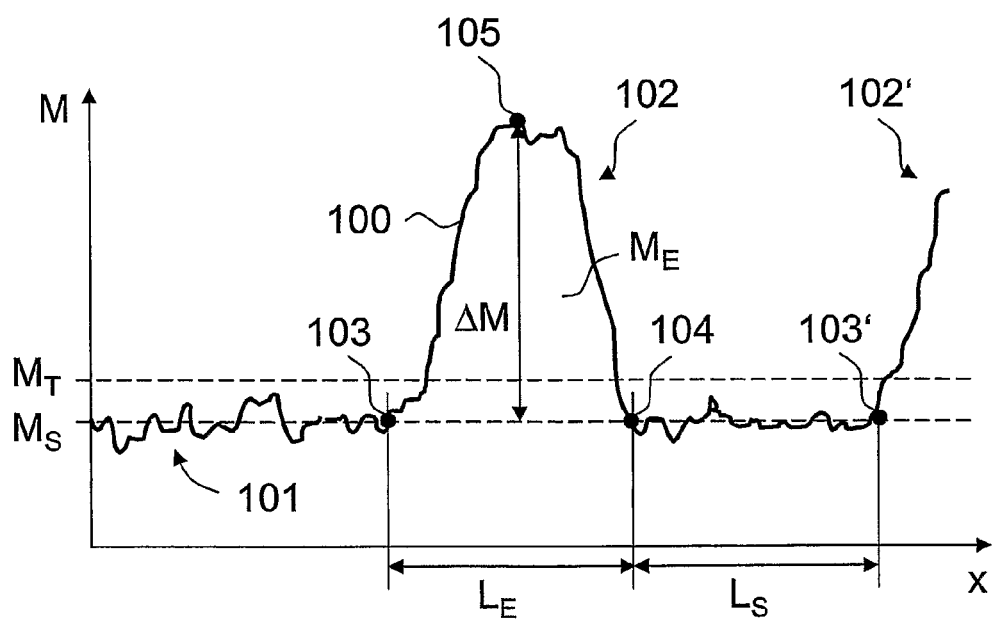
FIG. 4 shows an enlarged section of FIG. 2.

FIG. 4 shows a more detailed view of a section of the measurement curve M(x) of FIG. 2. Hereinafter, it is explained by way of FIG. 4 how further fancy yarn parameters such as slub length $L_E$, slub distance $L_S$, mass increase ΔM and slub total mass $M_E$ are evaluated.

For ascertaining a beginning 103 and end 104 of a slub 92, one previously determines a threshold value $M_T$ which is larger than the base yarn mass $M_S$. The threshold value $M_T$ may be predefined in a fixed manner—for example 110% of the base yarn mass $M_S$, automatically computed by the evaluation unit 3 or inputted by a user. The beginning 103 of a slub 92 is present if, proceeding from the noise floor 101, the threshold value $M_T$ is overshot. In order to exclude artifacts due to outliers, one may additionally control as to whether the overshoot persists over a predefined yarn length, i.e. whether a few further measurement points, which directly follow the measurement point exceeding the threshold value $M_T$, likewise lie above the threshold value $M_T$. In order to determine the beginning 103 of the slub 92 in a more accurate manner, one goes so far back on the measurement curve M(x) until, for the first time, a reading is smaller or equal to the base yarn mass $M_S$—or another predefined or computed value. This reading is defined as the beginning 103 of the slub 92. The end 104 of the slub 92 is ascertained mutatis mutandis in an analogous method: on undershooting the threshold value $M_T$ proceeding from the signal peak 102, one moves so far forwards on the measurement curve $M(x)$ until, for the first time, a reading is smaller or equal to the base yarn mass $M_S$. If required, one may use different threshold values for determining the slub beginning 103 and the slub end 104.

The slub length $L_E$ according to the present invention is defined as the distance between the beginning 103 and the end 104 of the slub 92. The slub distance $L_S$ is defined as the distance between the end 104 of a slub and the beginning 103' of a subsequent slub 92' to which a subsequent signal peak 102' belongs. The distance between two adjacent slubs 92, 92' is defined as the sum $L_E + L_S$ of slub length and slub distance. Typical slub lengths $L_E$ and slub distances $L_S$ lie in the range between 2 cm and a few meters.

The mass increase $\Delta M$ which corresponds roughly to a diameter increase of the fancy yarn 9 is defined in the simplest case as the difference between a local maximum 105 of the corresponding signal peak 102 and the base yarn mass $M_S$. Refined methods are possible for determining the mass increase $\Delta M$, which take account of the fluctuations of the scanning signal $M(x)$ along the slub length. Thus for example—analogously to the evaluation of the base yarn mass $M_S$ described above—the most common value within the corresponding slub length may be selected. A mean formation of values on the slub ridge is also considered. The mass increase $\Delta M$ is preferably specified as a multiple of the base yarn mass $M_S$, e.g. in percentage values, wherein the base yarn mass $M_S$ is preferably defined as 100%. Typical mass increases $\Delta M$ lie in a range between 20% and 500%.

A further parameter for characterizing a slub 92 is the so-called slub total mass $M_E$. This is essentially the difference between (i) the integral of the measurement curve $M(x)$ over the slub length $L_E$ and (ii) the mass $M_S \cdot L_E$ of the yarn body on this slub length $L_E$. The slub total mass $M_E$ may be determined by calculation by the evaluation unit 3. The yarn number of the slub 92 may be computed from the fancy yarn mass $M_E$, wherein the computation may contain a division of the slub total mass $M_E$ by the slub length $L_E$.

The shape of a slub 92 may also be determined and outputted. Thereby, one may fall back on a comparison with simple geometric shapes such as a bar, triangle, step, trapezium, or bell; cf. FIG. 18. The respective shape may e.g. be outputted on the output unit 4.

Not only are "local" parameters of the individual slubs of interest, but also "global" parameters of a whole yarn section, of a yarn or of a group of several yarns. Such a global fancy yarn parameter is the average yarn number (average yarn mass), which may be computed for example by way of mean formation over all readings. The yarn number of all base yarn 91 may also be of interest. A further global fancy yarn parameter is the average spatial frequency of the slubs, i.e. the average number of slubs per length unit.

The fancy yarn parameters mentioned above, and possible further ones are preferably determined dynamically during a running time of the scanning. The slub parameters are stored for the purpose of outputting. It is advantageous to additionally store a continuous running number allocated to the respective slub, in order not only to be able to provide information on the individual slubs, but also on their sequence.

It may be advantageous to equip the scanning unit 2 (FIG. 1) with a capacitive as well as an optical yarn sensor which may simultaneously measure one and the same yarn. The output signals of the capacitive and of the optical sensor may be linked to one another in a suitable manner for the purpose of an improved or more accurate evaluation. Capacitive measurement has the advantage that it provides a signal with a good signal-to-noise ratio. The signal however is proportional to the mass per length unit, and thus does not correspond to the visual impression of the yarn. This has a disadvantageous effect indeed with fancy yarn which in the region of a slub 92 often has a different yarn density than in the region of a base yarn 91. Optical measurement has the advantage of better representing the visual impression of yarn, because it measures essentially the visible yarn diameter and it is therefore better suitable to fabric simulations. For this, the optical measurement signal has a greater noise than the capacitive measurement signal. It is possible by way of suitable linking of the two output signals, to profit from the advantages of both measurement types and to eliminate or at least weaken their respective disadvantages.

Results of the evaluation may on the one hand be variables such as e.g. minima, maxima, arithmetic means and/or standard deviations of the above defined fancy yarn parameters. The number of slubs 92 per yarn length may be a further variable of interest. These variables may be outputted as alphanumeric signs. On the other hand, the results of the evaluation may be graphically represented and outputted on the output unit 4 in a suitable manner. Preferred presentation types are shown in the FIGS. 5-11.

Figure 5A:
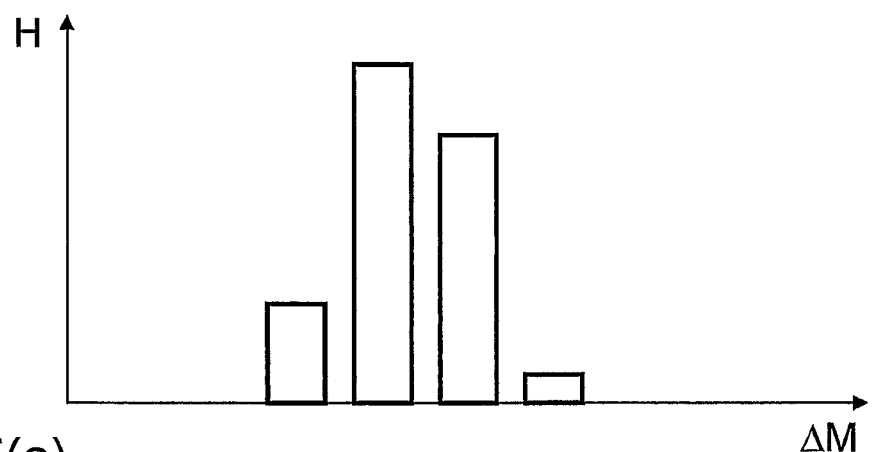
Figure 5B:
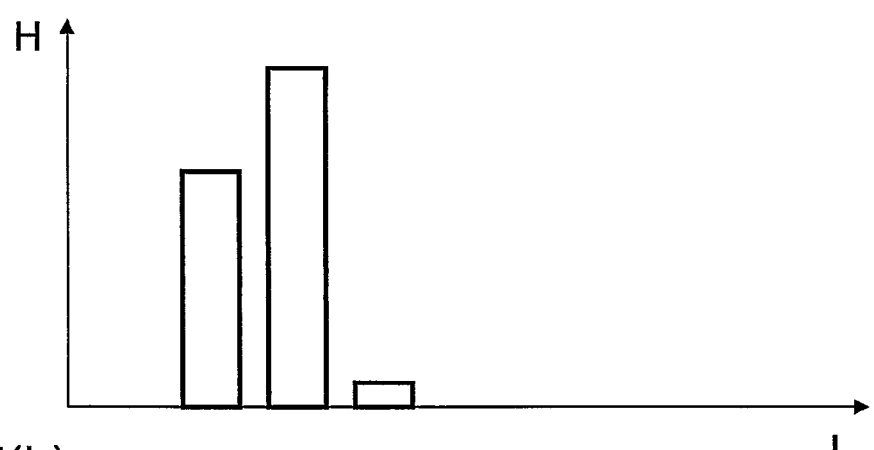
Figure 5C:
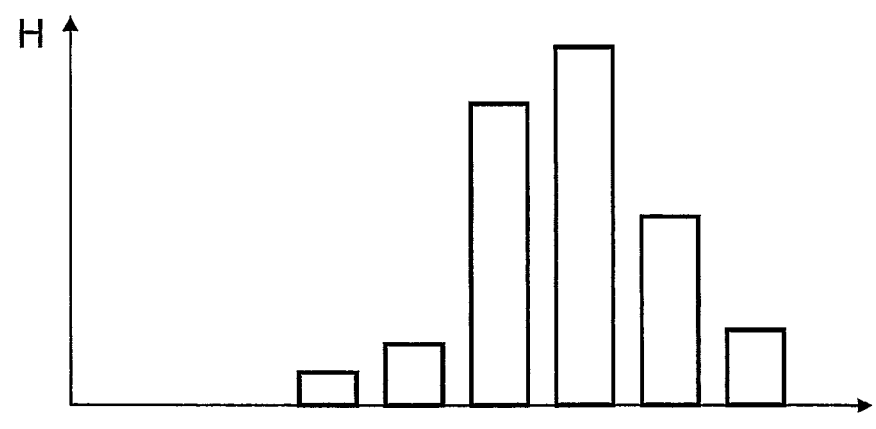

One possible representation type is a histogram, i.e. the graphic representation of the class frequencies of the classed yarn parameters. Three examples in the form of bar charts are specified in FIG. 5. The ordinate in each case is the frequency H. In FIG. 5(a) the mass increase $\Delta M$, in FIG. 5(b) the slub length $L_E$, and in FIG. 5(c) the slub distance $L_S$ have been use as the abscissa. The abscissas may have a linear, logarithmic or other division. The division and/or scale of the axes may be automatically computed or may be selected by way of input on the part of an operating person. The same applies to the selection of the classification, i.e. to the width of the classes. Not all classes necessarily need to have the same width.

Figure 6A:
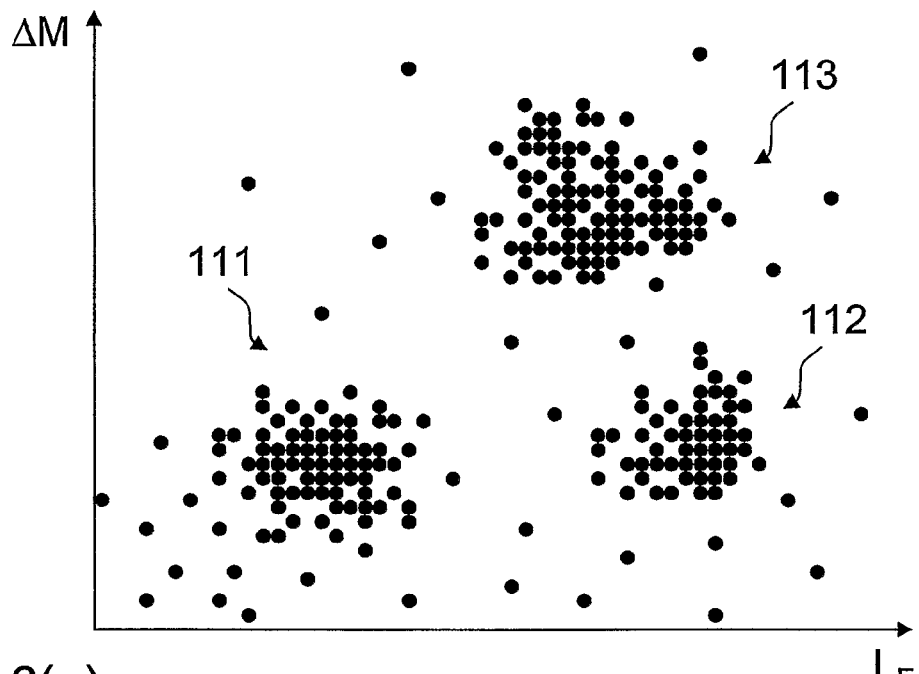

The representation manner of FIG. 6 is a so-called scatter diagram (aggregate of plots). In this, the mass increase $\Delta M$ is plotted against the slub length $L_E$ for all slubs 92 of an fancy yarn 9 or a yarn section. Each slub 92 is plotted as a point at the correct location. This representation simplifies the division of different slubs 92 into different classes. Thus for example, it is immediately evident from FIG. 6(a), that the examined fancy yarn 9 has three classes 111-113 or populations of slubs 92:

a first class 111 with short, low slubs
a second class 112 with long, low slubs, and
a third class 113 with long, high slubs.

Figure 6B:
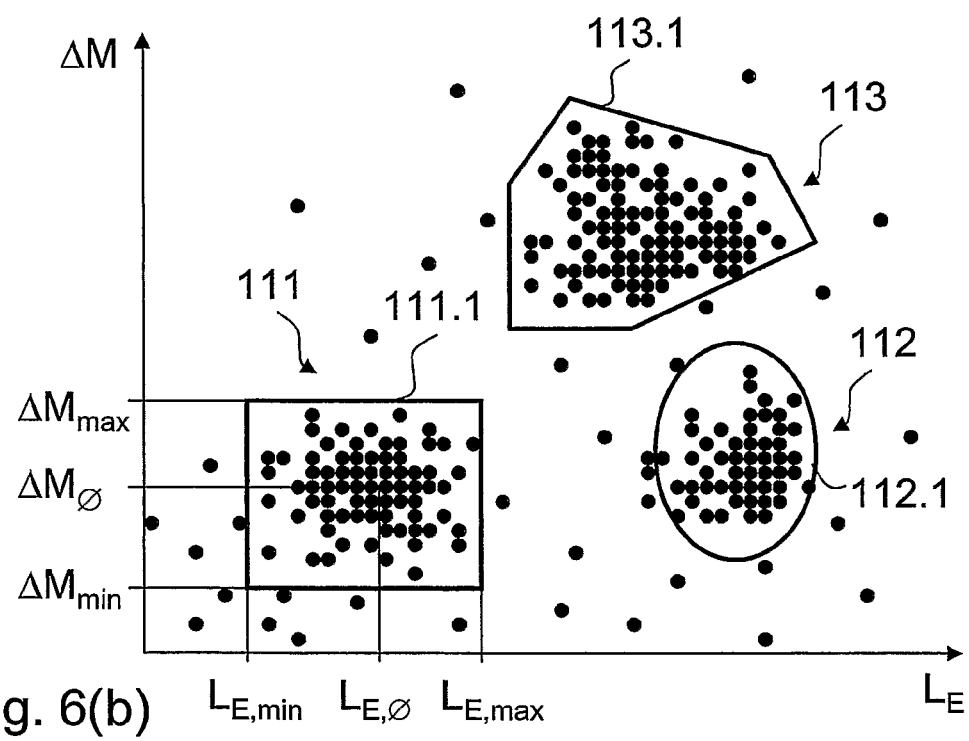

An outlier analysis is carried out by way of the scatter diagram of FIG. 6(a). For this purpose, one may provide a tool in order to define slub populations 111-113 and to the delineate them from one another as well as from outliers. Such a tool may e.g. permit part surfaces 111.1-113.1 of the scatter diagram to be defined on a monitor with a mouse, as is represented in FIG. 6(b). One slub population 111-113 is allocated to each part surface 111.1-113.1. The part surfaces may e.g. be shaped as a rectangle 111.1, as a circle 112.1 or a polygon 113.1. Points lying outside the part surfaces 111.1-113.1 are to be graded as outliers and with further evaluations and/or representations, may be characterized as such or not taken into account. If no part surfaces are defined, then all points of the scatter diagram are counted as slubs and are treated as such.

Other scatter diagrams are possible, for example slub total mass $M_E$ against slub length $L_E$, slub total mass $M_E$ against mass increase $\Delta M$, etc. The scatter diagram may be issued in a colored manner, wherein different colors may indicate different measurements, different point densities and/or populations or outliers (cf. FIG. 10). A three-dimensional representation is analogously possible, in which two coordinates correspond to those of FIG. 6, and the third coordinate corresponds to the point density; cf. FIG. 9.

The scatter diagram may be represented for an individual fancy yarn sample or for several fancy yarn samples. In the latter case, one may use different colors for the different fancy yarn samples, in order to display possible differences between the samples. With several fancy yarn samples, one may display the result of the entirety of all fancy yarn samples additionally to the results of the individual fancy yarn samples, preferably in a color which is individually allocated.

Apart from the actual values, one may also represent nominal values or nominal regions for one or more classes of slubs on the scatter diagram. The nominal and actual values may also be compared in other representation types, or in a purely numeric manner. Such nominal-actual comparisons permit e.g. a control on the quality of a copy (actual value) or a predefined fancy yarn (nominal value).

The results may also be issued in the form of a table or a classification matrix—as shown in FIG. 7, instead of a scatter diagram. The table axes correspond to the axes of the scatter diagram of FIG. 6. The numbers of respective slubs 92 are entered into the fields of the tables. Alternatively to the absolute number of slubs 92, one may also indicate their relative share; e.g. in percent or per thousand. Each table field thus represents a class of slubs 92, analogously to the classes 111-113 which are described on the occasion of FIG. 6. The selected size of the table fields is directed to the desired classification. With the selection of the size of the table fields, one should also take note that the resolution is sufficiently fine, but that the table still remains clear. In the example of FIG. 7, relatively small table fields were selected, which permit a finer classification than the three classes 111-113 which were described on the occasion of FIG. 6. The table fields may be filled with colors, patterns or steps of gray, which in turn are allocated to different numbers of slubs 92, for the purpose of an improved visualization.

With the scatter diagram (FIG. 6) as well as the classification matrix (FIG. 7), the axes, independently of one another, may have a linear, a logarithmic or other division. The division and/or scale of the axes may be computed automatically, or may be selected by way of input on the part of the operating person. The same applies to the width and height of the table fields in the classification matrix of FIG. 7, i.e. for the selection of the classification. FIG. 8 shows a further preferred output possibility for the determined fancy yarn parameters. It is the case of a table which is subdivided into five main columns for the five parameters of slub length $L_E$, slub distance $L_S$, mass increase $\Delta M$, diameter increase and number # of the slubs. The first four main columns for their part are subdivided in each case into three sub-columns for the minimum Min, the mean Ø and the maximum Max of the respective parameter. The lines of the table may contain the values for the entire yarn or for the entire examined yarn section, as well as for the individual slub populations 111-113. The minima $L_{E,min}$, $\Delta M_{min}$, the means $L_{E,\varnothing}$, $\Delta M_\varnothing$ and the maxima $L_{E,max}$, $\Delta M_{max}$ are indicated for the population 111 in FIG. 6(b). Of course, the table may also be formed in a different manner. In any case, such a tabular representation of the determined fancy yarn parameters leads to a reduction of data. Particularities of the fancy yarn concerned may be very quickly detected and different fancy yarns may be easily compared by way of the table.

Figure 9:
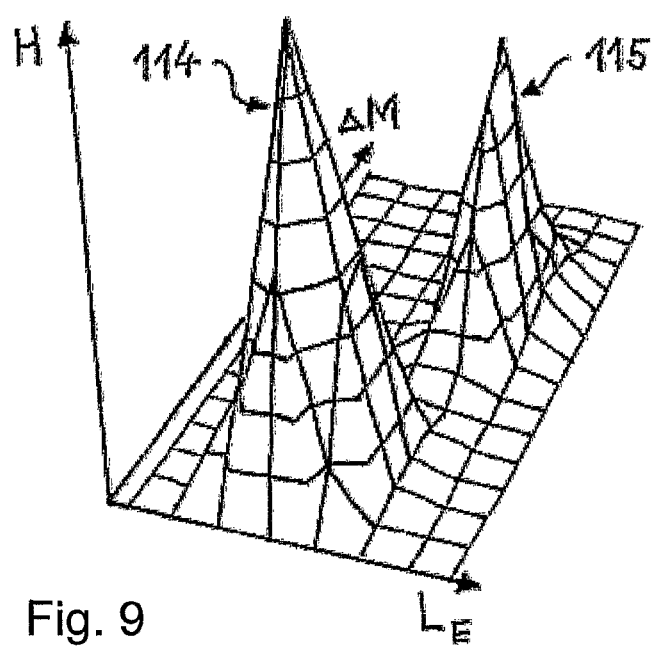

A further manner of representation for the results of the evaluation of fancy yarn parameters is shown in FIG. 9. It is the case of a surface in three dimensions (3D). Two of the three dimensions, the two horizontal axes, correspond to the slub length $L_E$ and the mass increase $\Delta M$, as in the scatter diagram of FIG. 6. The third, vertical dimension indicates the respective frequency H of the measured values, i.e. the point density in the scatter diagram of FIG. 6 or the numbers of FIG. 7. The 3D-surface which arises in this manner gives the impression of a mountain [range] which permits a rapid and memorable visual perception of the peculiarities of the respective fancy yarn 9. It is particularly a synoptic comparison of two such "mountains" which very quickly shows whether the fancy yarn concerned has similar or different characteristics, and in the latter case where the main differences lie. It is to be noted that the example of FIG. 9 relates to a different fancy yarn than the example of FIG. 6. Whilst the fancy yarn of FIG. 6 has three classes 111-113 of slubs 92, the fancy yarn of FIG. 9 only has two of them 114, 115.

Figure 10:
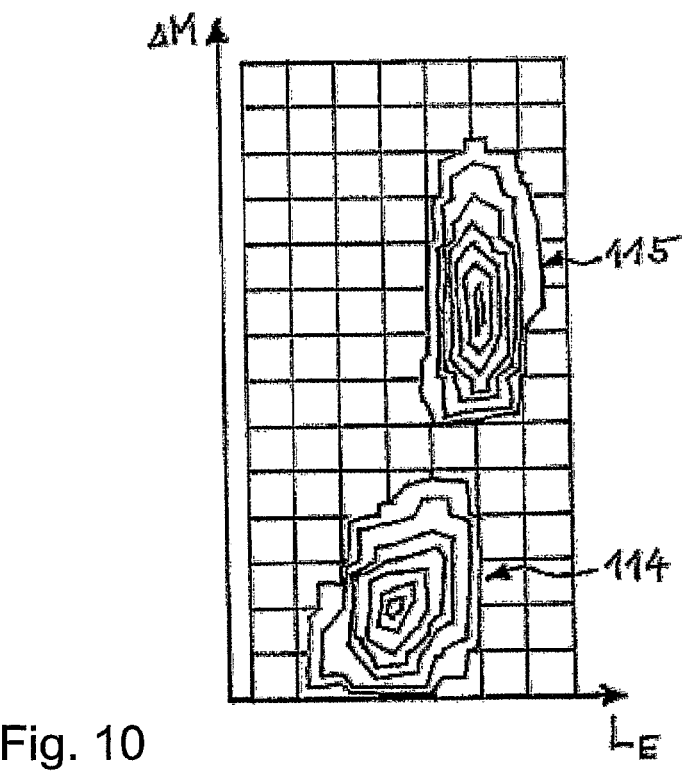

The three-dimensional representation manner of FIG. 9 may be reduced also to two dimensions. FIG. 10 shows such a diagram which arises by way of the projection of the "mountain" of FIG. 9 into the plane spanned by the two horizontal axes $L_E$, M. A "map" thus arises on which the "mountains" 114, 115 of FIG. 9 are represented by way of "altitude contours", i.e. lines of the same frequency H. Instead of "altitude contours", one may apply colors or cross-hatchings for rendering the different frequencies H visible.

The representation types of the FIGS. 5-10 do not take into account information on the sequence of the individual slubs. This information is completely present in the measurement series as is represented in FIG. 2. It is possible from this to determine the respective yarn parameter such as mass increase, slub length and slub distance as the measurement variables (number value x unit), and to list these measurement variables in the sequence of their occurrence, after one another. Such an alphanumeric listing of the reduced measurement data may be useful for certain cases, but is however less clear. Information on the sequence of the individual slubs is fully contained in the representation manner of FIG. 11, wherein graphics have the advantage of an improved clarity and visual perception compared to an alphanumeric value table. A horizontal bar is drawn in for each slub 92 and an adjacent base yarn 91. The bar is composed of two parts. The length of a first, left part indicates the respective slub length $L_E$, the length of a second, right part indicates the respective slub distance $L_S$. The next bar lying therebelow characterizes the subsequent slub, etc. The horizontal bars of FIG. 11 may of course also be replaced by vertical columns. Measurement variables other than lengths $L_E$, $L_S$ may be plotted as bars, e.g. a slub mass and the associated base yarn mass, which may be advantageous in particular with structured yarn with different base yarn masses. It is also possible for a bar or column to indicate more than two slub parameters, e.g. with multi-step slubs (see FIG. 16) the first slub length $L_{E,1}$, the second slub length $L_{E,2}$ and the associated slub distance $L_S$.

Figures 11, 12:
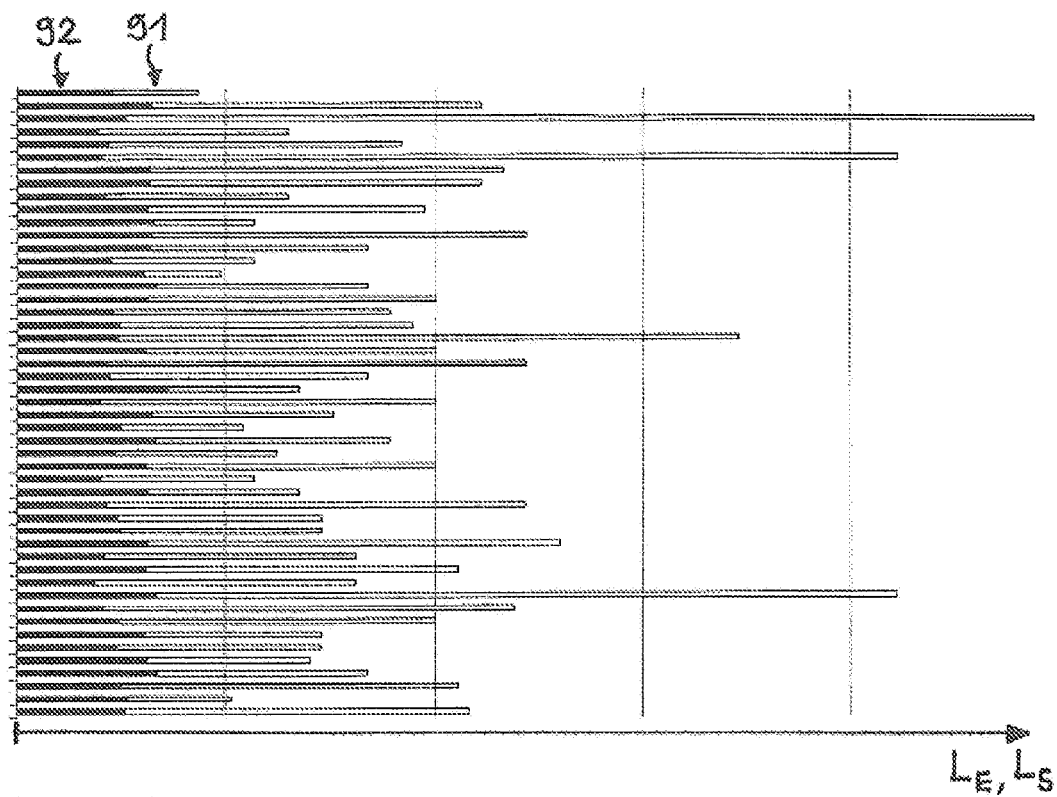

FIG. 12 shows a manner of representation which at least represents a part of the information on the sequence of the individual slubs in a clear manner. It is the case of a classification matrix which assumes a classification of the slubs as has been implemented with the classes 111-113, somewhat as in FIG. 6. In each case, a pair of two adjacent slubs 92, 92' are considered, of which a first slub 92 is called a "leading slub" and a second slub 92' a "trailing slub". A corresponding entry into the classification matrix of FIG. 12 whose horizontal axis indicates the leading slub 92 and whose vertical axis indicates the trailing slub 92' is effected for each pair 92, 92'. One may deduce from the fictive example of FIG. 12, that in practice, two slubs of the first class 111 (cf. FIG. 6), and two slubs of the second class 112 are never successive, but that a slub of the first class 111 often follows a slub of the second class 112, and a slub of the third class 113 very often follows a slub of the first class 111.

Figure 13:
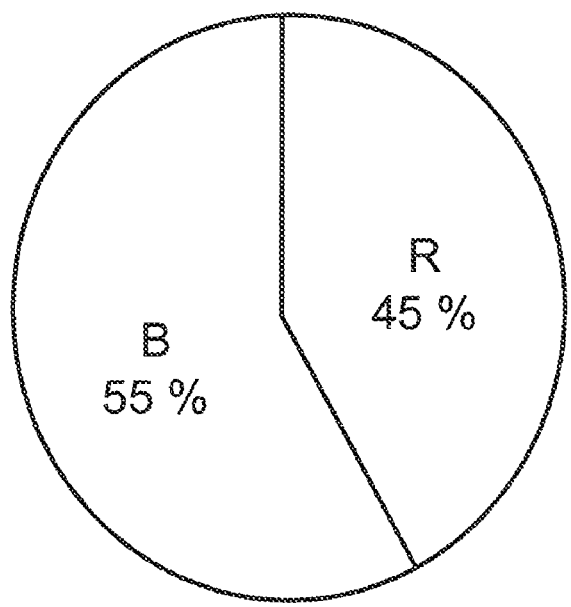

Various slubs of a fancy yarn 9 may have different colors. For this reason, it may be desirable to obtain information on the color of the fancy yarn 9. Suitable scanning units 2 and evaluation units 3 (see FIG. 1) from the state of the art mentioned above are known for this. One possible representation manner for the obtained color information is shown in FIG. 13. Here it is the case of a circular chart which indicates the measured shares of the differently colored slubs. In the example of FIG. 13, the fancy yarn contains red (R) and blue (B) slubs which occurred with a frequency of 45% and 55% respectively. An enhancement to more than two colors is of course also possible. In the case that the output unit 4 (see FIG. 1) permits a colored output, the individual circle segments may be issued in the corresponding color. A pie chart is also possible instead of a circular chart.

Figure 14:
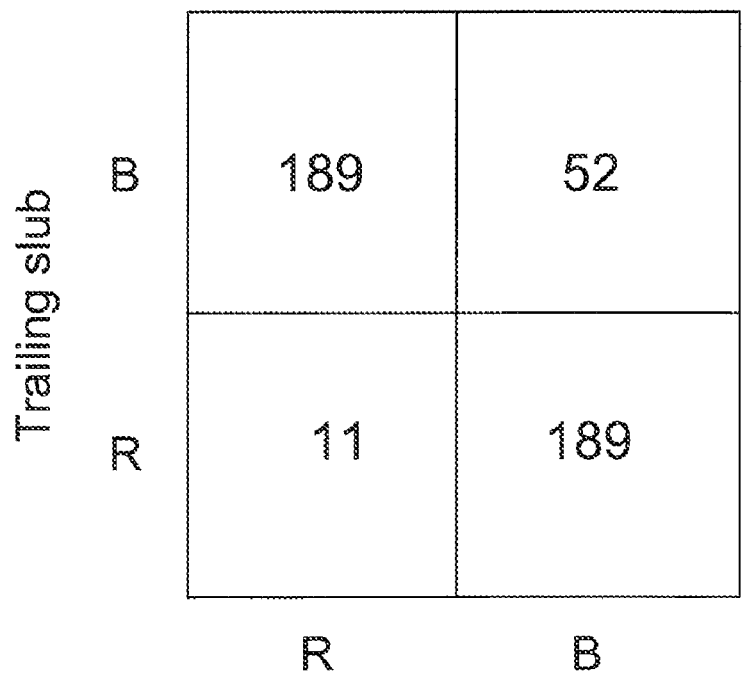

The circular chart of FIG. 13 contains no information on the sequence of the color slubs. This information is at least partly present in the representation manner of FIG. 14. Analogously to FIG. 12, in each case two successive slubs are considered, and the frequency of their colors R, B is plotted in the table, wherein the horizontal table axis indicates the color R, B of the leading slub, and the vertical axis indicates the color R, B of the trailing slub. One may deduce from the table of FIG. 14 that a color change often occurs in this fictive example, whereas two adjacent slubs having the same color is rather rare.

Figure 15A:
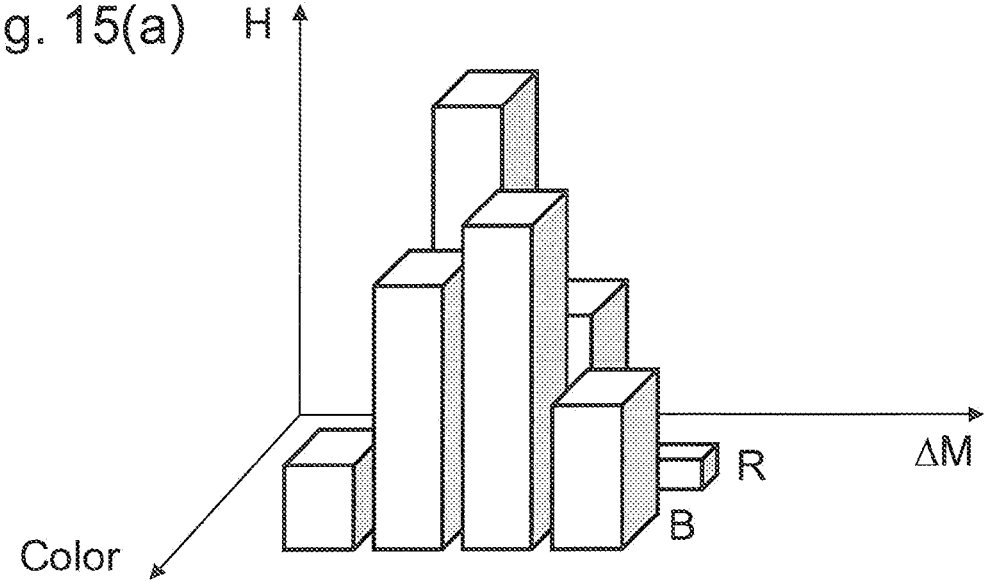
Figure 15B:
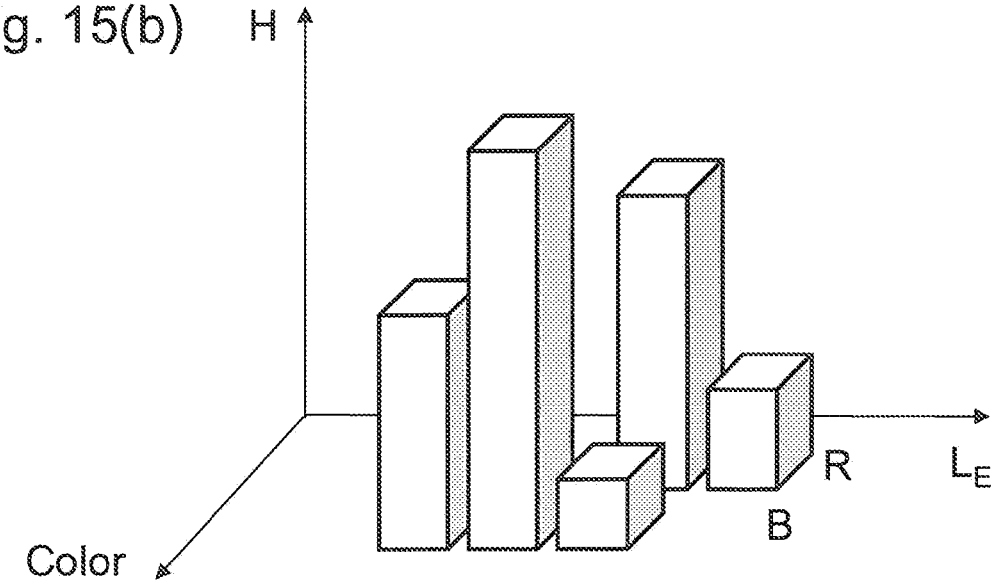

The three-dimensional column charts of FIG. 15, by way of fictive examples, show how the color information may be combined with the geometric information in a single representation manner. Thereby, the geometric information lies in the plane of the drawing and corresponds to that of FIG. 5(*a*) and FIG. 5(*b*) respectively. The frequency of classes of the mass increase ΔM is plotted in the diagram of FIG. 15(*a*), and the frequency of classes of the slub length $L_E$ is plotted in the diagram of FIG. 15(*b*). The third dimension is used for the color information R, B. One may deduce from the diagram of FIG. 15(*a*) that the red slubs R tend to have smaller mass increases ΔM than the blue slubs B. The diagram of FIG. 15(*b*) indicates that the red slubs R tend to be longer than the blue slubs B.

The FIGS. 5-15 discussed above only indicate a few example for representing the fancy yarn parameters of mass increase ΔM (or diameter increase), slub length $L_E$, slub distance $L_S$ and color. One may of course also graphically represent further relations between these and further fancy yarn parameters in a similar and two-dimensional or three-dimensional manner.

Whilst single-step slubs have been discussed up to now, multi-step slubs are considered hereinafter. One example of a series of readings on a two-step fancy yarn is specified in FIG. 16, in the same representation as FIG. 4. Here one may differentiate between a first slub step with a first slub total mass $M_{E,1}$ per length unit, a first mass increase $\Delta M_1$ and a first slub length $L_{E,1}$, and a second slub step with a section slub total mass $M_{E,2}$ per length unit, a second mass increase $\Delta M_2$ and a second slub length $L_{E,2}$. The mentioned parameters may be determined in a manner which is analogous to that described for a single-step fancy yarn.

Figures 16, 17:
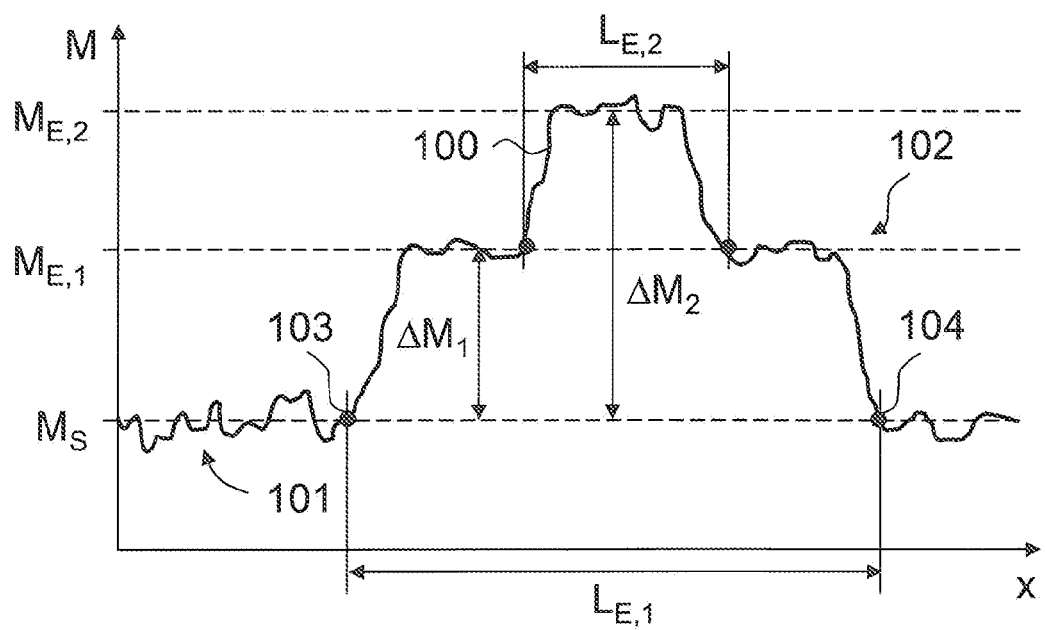
FIG. 16 shows an example of a series of reading with regard to a two-step fancy yarn, in the same representation as FIG. 2.
FIG. 17 shows one possible representation type according to the invention, for outputting the characteristics of a multi-step yarn.

One possible manner of representation for the parameters of multi-step fancy yarn is shown in FIG. 17. Here it is the case of a table whose horizontal axis corresponds to the classed mass increase ΔM; cf. FIG. 5(*a*). The lines of the table represent the different steps of the fancy yarn. The respective frequencies are plotted in the fields of the table. The fancy yarn is two-step in the fictive example of FIG. 17, wherein the second step occurs in two variants: with a relatively small mass increase $\Delta M_2$ on the one hand, and with a relatively large mass increase $\Delta M_2$ on the other hand. An analogous manner of representation is also possible for the slub length $L_{E,1}, L_{E,2}, \ldots$.

A further parameter of fancy yarn is the so-called pattern length. This is the length of the shortest sequence of slubs which are periodically repeated in the fancy yarn. There is no periodicity whatsoever within this sequence, i.e. at least one slub parameter such as e.g. the slub distance $L_S$ is random or pseudo-random. The pattern length may be obtained e.g. by way of correlation computation from readings, as they are represented for a short yarn section in FIG. 2. Such a correlation computation with all readings may be extensive with regard to computation. In order to reduce the computational effort, the measurement data may be previously reduced in that e.g. the respective yarn parameters such as mass increase, slub length and slub distance are determined and the correlation computation is based on this reduced data. In an analogous manner, one may also obtain information on the presence of—mostly undesired—sub-patterns and their lengths. The pattern length and/or sub-pattern lengths are preferably issued in alphanumeric or graphic form.

Figure 18:
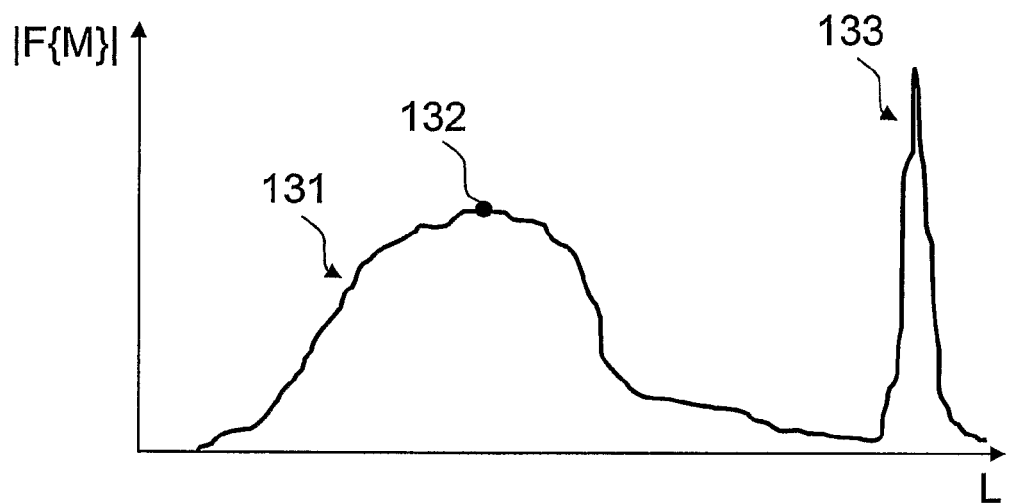
FIG. 18 shows a spectrogram of a series of readings with regard to a fancy yarn.

A spectrogram of the measurement signal M(x) of FIG. 2 may also provide useful information on the fancy yarn. The measurement signal M(x) is preferably subjected to a Fourier transformation for determining the spectrogram. One fictive example of a spectrogram |F{M}| or more precisely of the real part of the Fourier transform is shown in FIG. 18, wherein as is customary, a period length L is selected as the abscissa, preferably in a logarithmic scale. Usually, the spectrogram |F{M}| displays a relatively broad distribution 131 of the spatial frequencies or of the period lengths L. One may deduce an average distance of the slubs from the position of the maximum 132. A pronounced peak in the spectrogram |F{M}| would indicate a—mostly undesired—periodicity in the fancy yarn. The periodicity on the one hand may relate to the individual slubs. With a fancy yarn with a constant slub distance $L_E+L_S$, within which the slub length $L_E$ and the slub distance $L_S$ vary, the maximum 132 appears as a pronounced peak. In order to ascertain this, a yarn length of at least ten, preferably one hundred and more slub distances should be measured. The periodicity on the other hand may relate to the patterns. With a sufficiently long measurement series—at least ten, but preferably one hundred and more pattern lengths—one may also read out the pattern length from the position of a respective peak 133 in the long-waved region of the spectrogram |F{M}|.

Figure 19:
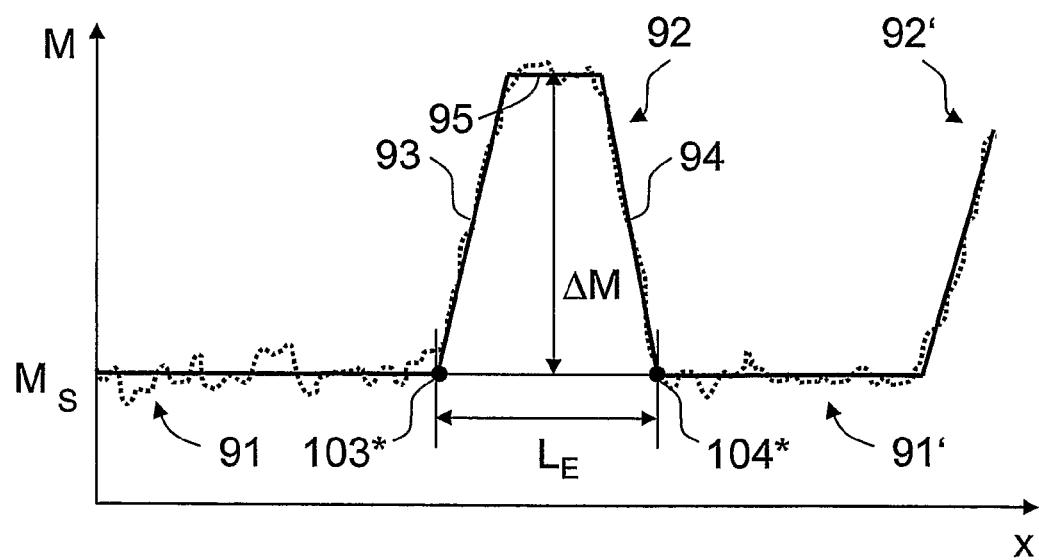
FIG. 19 shows a measured and an idealized slub.

A further graphic representation manner for the slubs is a smoothed or idealized representation of the readings, as is shown in FIG. 19. On the one hand, the readings of FIG. 4 are drawn in a dotted manner. On the other hand, an idealized course of the measurement curve is indicated with an unbroken line. As the man skilled in the art knows, there are many possibilities of obtaining an idealized curve in the manner of FIG. 19 from a real measurement curve. In the application example of FIG. 19, base yarn 91, 91' have been approximated by horizontal straight lines which all lie at the height of the previously determined base yarn mass $M_S$. One slub 92 is idealized in each case as a trapezium with flanks 93, 94 and a horizontal roof 95. Thereby, the trapezium does not necessarily need to be symmetrical, i.e. the flanks 93, 95 with regard to magnitude may also have different gradients. The approximation of the slub 92 by a trapezium may be effected according to methods and criteria known to the man skilled in the art. The flanks 93, 94 may roughly be straight lines whose positions have been determined by way of the method of least squares, or in another manner. The height of the trapezium, i.e. the position of the roof 95, may be determined according to the criterion that the area of the trapezium is equal to the area below the real measurement curve. The slub length $L_E$ may for example be defined as the base length of the trapezium, i.e. as the distance between a slub beginning 103\* and a slub end 104\*, wherein the slub beginning 103\* and the slub end 104\* are the intersection points of the horizontal representing the base yarn mass $M_S$ and the left flank 93 or the right flank 94. Alternatively, the slub length $L_E$ may be may be defined as the width of the trapezium at half the height, which is equal to half the sum of the base length and the roof length. The mass increase $\Delta M$ may be defined at the height of the trapezium, i.e. as the distance between the base and the roof. Under certain circumstances, the trapezium may degenerate into the special case of a triangle (trapezium with a roof length equal to zero) or of a rectangle (trapezium all with right angles). Other shapes for the idealized measurement curve are likewise possible. Such idealized courses of curves permit an improved visual perception of the characteristics of the fancy yarn. Parameters of the idealized curve, such as e.g. height, base length, roof length, the slub length $L_E$ or the flank gradients of the trapezium may be outputted as characteristic variables in a table for example, and be used for further evaluations. The output of such variables leads to a reduction in the data.

Figure 20:
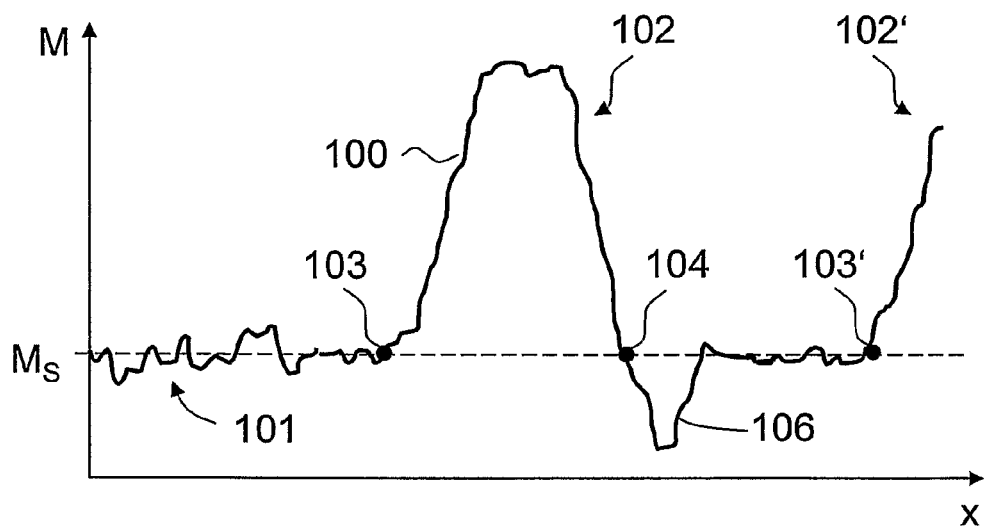
FIG. 20 shows a measurement curve with a thin place, analogous to FIG. 4.

An incomplete manufacturing process for the fancy yarn may lead to a thin place 106 being present directly next to a slub 102, as indicated in FIG. 20. Such undesired thin places 106 may be detected according to the present invention. Their number or share with regard to quantity at the slubs 102 may be outputted as a result. A thin place share of 50% means that a thin place 106 was observed next to half of all slubs 106, which indicates a deficient manufacturing process.

Spinning works which manufacture fancy yarn have the need to differentiate between the following two phenomena:
on the one hand, the virtual base yarn manufacture, which may introduce imperfections, irregularities and faults such as thick places or thin places into the yarn, and
on the other hand, the slub manufacture which incorporates the desired slubs onto the virtual base yarn, e.g. in the form of thickenings.

These two phenomena are sometimes impossible or difficult to differentiate with conventional yarn testing methods and apparatus. The exemplary curve of FIG. 4 was selected for didactic reasons, so that it is quite clear from this, what a slub 102 is and what a base yarn 101 is. In practice however, the undesired thickness fluctuations on the base yarn 101 may be so large, that they exceed the threshold value $M_T$ and as a result are wrongly considered to be a slub on evaluation. The results of the evaluation are therefore adulterated. The results of this may lead to the wrong measures being taken in the manufacturing process. If e.g. long thick places or yarn mass fluctuations are assumed to be small slubs, the part process for slub manufacture is changed such that larger slubs may be produced. This measure unnecessarily changes the slub structure without alleviating the actual cause of the fault—perhaps a defect in one path.

Figure 21:
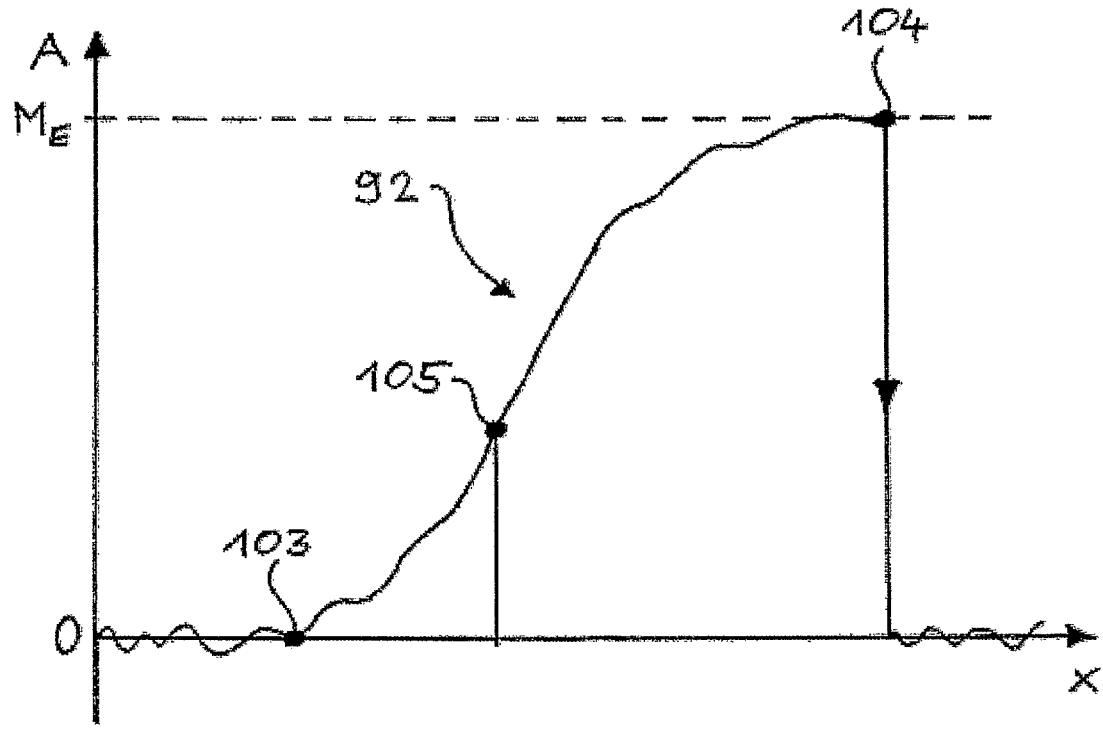
FIG. 21 shows the course of the area below a measurement curve, as a function of the length coordinate.

Here, a preferred embodiment solves this problem by way of specifying the definition of a slub. The method described on the occasion of FIG. 4 may be disadvantageous since on setting the threshold value $M_T$, it only takes into account a one-dimensional mass increase. As described, although one may attempt to reduce this disadvantage by way of the demand that the excess must last for a certain length. This however also does not lead to an optimal recognition of the slubs. The observation of an area below the measurement curve—or what is considered here as being equivalent to the area, a certain integral of the measurement curve, has been shown to be more advantageous. Such an area may be computed at least approximately with one of the known numeric integration methods, like with the rectangle or trapezium method. FIG. 21 schematically shows a typical course of the area $A(x)$ computed in this manner, as a function of the length coordinate x, wherein the previously determined base yarn mass $M_S$ (see FIG. 4) serves as basis for determining the area. The values of $A(x)$ fluctuate around the value zero in the region of the base yarn 101. Any thick places, even if they have a large mass increase, do not cause any significant area changes, since they only extend in each case over a short length interval. A real slub 92 differs from a thick place in that it causes a significant rise of the curve $A(x)$ which sets in at the beginning of a slub 102. A local maximum 105 of the slub 92 which may also be described as the position of the slub 92, is located at the turning point of the curve $A(x)$. After the slub end 104, the curve $A(x)$ again fluctuates around a constant value, which indicates the slub total mass. If one ascertains such a slub end 104, then the further course of the curve may be set back to the value zero by way of subtraction of the value $M_E$. A further base yarn follows etc. All slubs and their positions may be recognized in a reliable and stable manner and be differentiated from thick places by way of this.

The ascertaining of a slub is preferably made dependent on the simultaneously fulfillment of several criteria, e.g. of the following three criteria:
(i) exceeding a predefined threshold value for the area $A(x)$,
(ii) exceeding a predefined threshold value for the slub length $L_E$, and
(iii) exceeding a predefined threshold value for the mass increase $\Delta M$.

Only when these criteria are simultaneously fulfilled may one reliably assume that a proper slub and not a yarn imperfection is present.

The differentiation between the virtual base yarn and slubs is simplified even greater by way of a further embodiment of the method according to the invention. According to this embodiment, the idealized course of the curve according to FIG. 19 is subtracted from the real measurement curve. This is schematically represented in FIG. 22. In this, FIG. 22(*a*) shows the curve of the original readings, FIG. 22(*b*) the idealized curve (cf. FIG. 19), and FIG. 22(*c*) the curve which arises when one subtracts the idealized curve from the original measurement curve. The curve of FIG. 22(*b*) shows only the (idealized) slubs, the curve of FIG. 22(*c*) only the virtual base yarn without slubs. These representations alone may contribute to a deeper understanding of the structure of the examined fancy yarn. The data obtained in this manner may however be evaluated even further, as is discussed hereinafter.

Figure 22A:
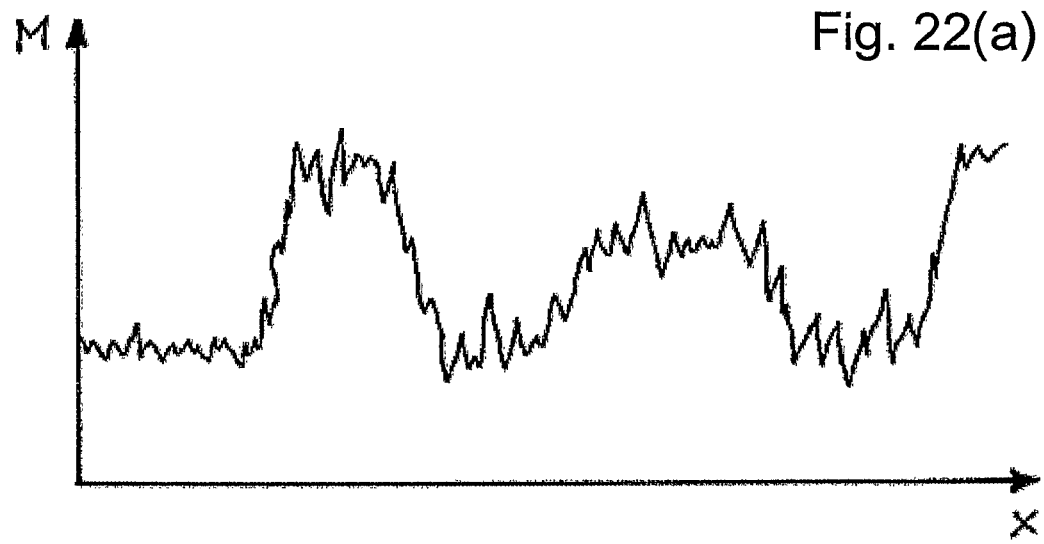
FIG. 22 shows the mass per length unit as a function of the length coordinate, (a) for the measurement curve, (b) for an idealized curve and (c) for a curve which arises by subtraction of the curve (b) from the curve (a).
Figure 22B:
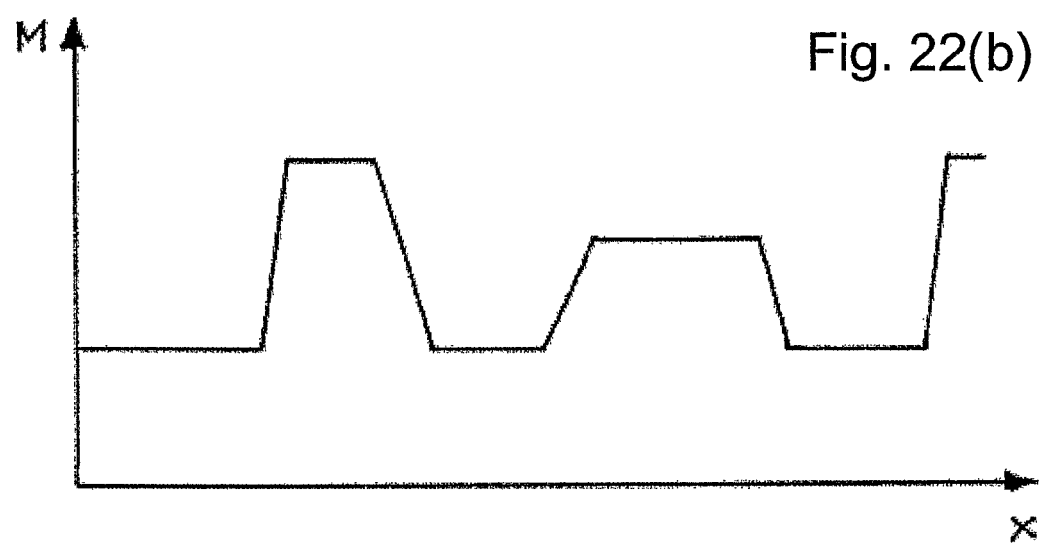
Figure 22C:
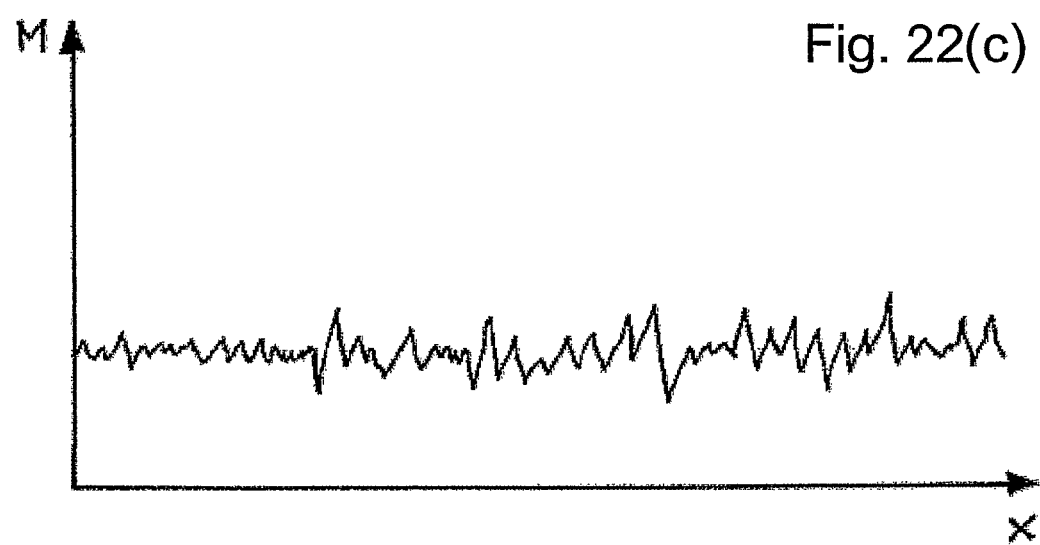
Figure 23A:
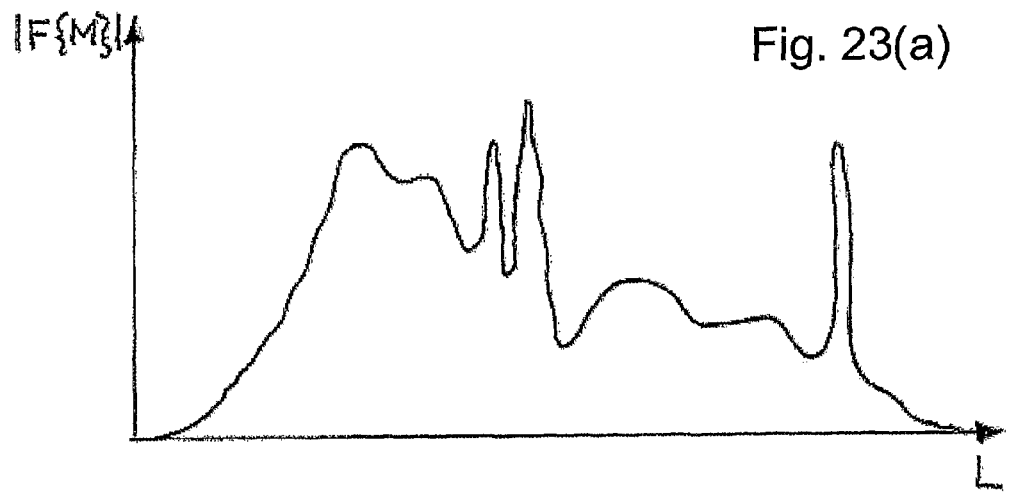
FIG. 23 shows spectrograms (a) of the curve of FIG. 22(a), (b) of the curve of FIG. 22(b), and (c) of the curve of FIG. 22(c).
Figure 23B:
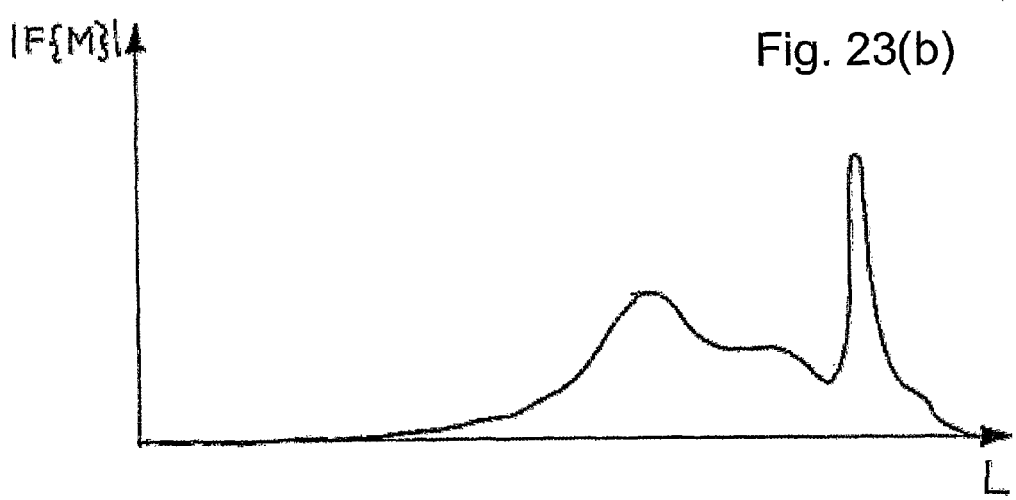
Figure 23C:
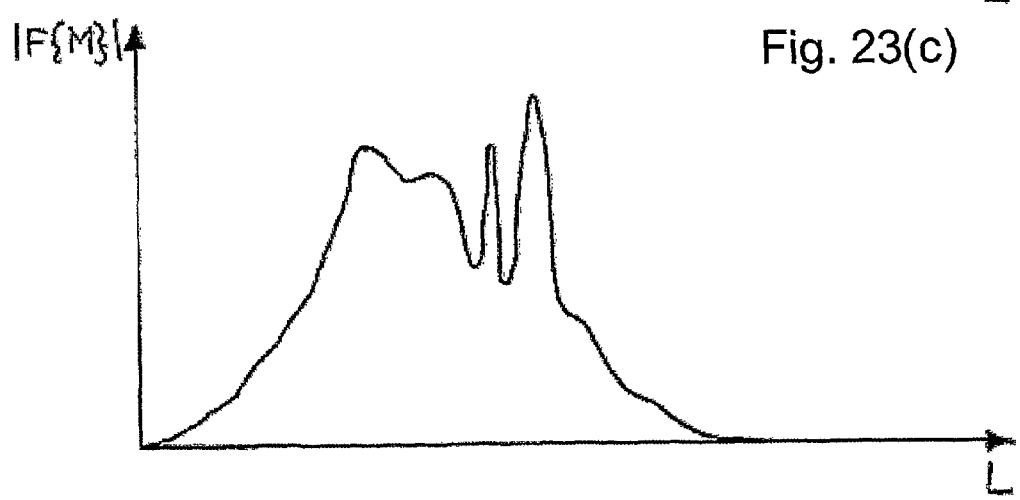

FIG. 23 schematically shows results of an evaluation of the data of FIG. 22 in a spectrogram, i.e. in a representation which corresponds to that of FIG. 18. FIG. 23(*a*) shows the spectrogram of the original readings, i.e. the curve of FIG. 21(*a*). As already indicated above, it is difficult or even impossible to differentiate between slubs and virtual base yarn only by way of this spectrogram. The representations of the FIGS. 23(*b*) and (*c*) alleviate this problem. FIG. 23(*b*) shows the spectrogram of the slubs alone, i.e. of the curve of FIG. 22(*b*). This data related to the slub permits malfunctioning in the slub production to be localized and overcome in a targeted manner, or permits the slub production to be changed in a targeted manner. Peaks in the long-waved region may e.g. indicate undesired periodicities, which may be avoided with suitable measures. FIG. 23(*c*) shows the spectrogram of the virtual base yarn, i.e. of the curve of FIG. 22(c). Any peaks in this spectrogram give good hints as to certain faults in the spinning process, or in the process stages preceding the spinning process, such as eccentricities of certain rollers in the drawing arrangement. These faults may be localized by way of the respective wavelengths in the spectrogram of FIG. 23(c), and subsequently dealt with.

Figure 24A:
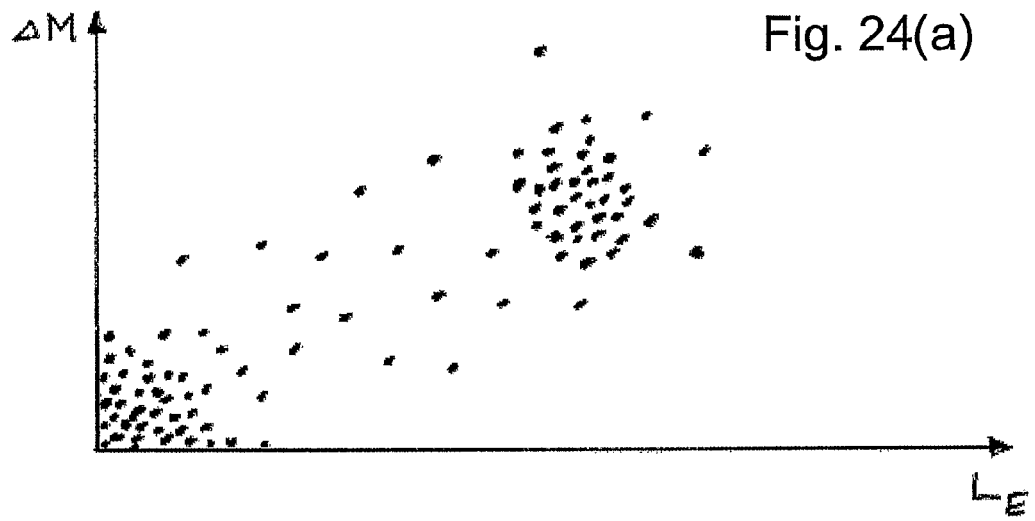
FIG. 24 show scatter diagrams (a) of the readings of FIG. 22(a), (b) of the slubs of FIG. 22(b), and (c) of the virtual base yarn of FIG. 22(c).

The data of FIG. 22 may just as easily be represented in a scatter diagram, analogously to FIG. 6. This form of representation may also be very useful in order to differentiate between slubs and the virtual base yarn. A schematic example is specified in FIG. 24. FIG. 24(a) shows a scatter diagram of the original readings of the curve of FIG. 22(a). Here, three phenomena intermingle:

the lesser disturbing thick places occurring in each yarn,
slubs and
thick places wrongly evaluated as slubs.

Figure 24B:
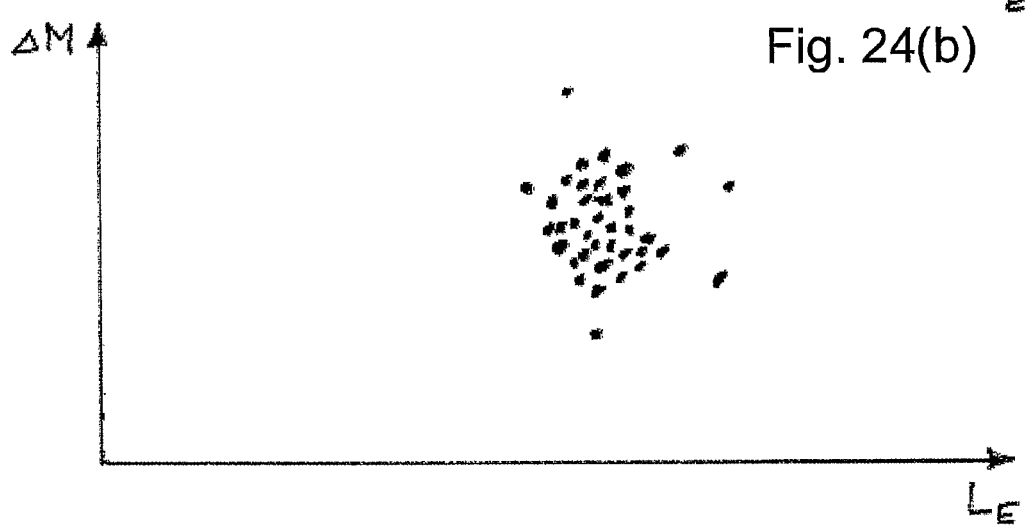
Figure 24C:
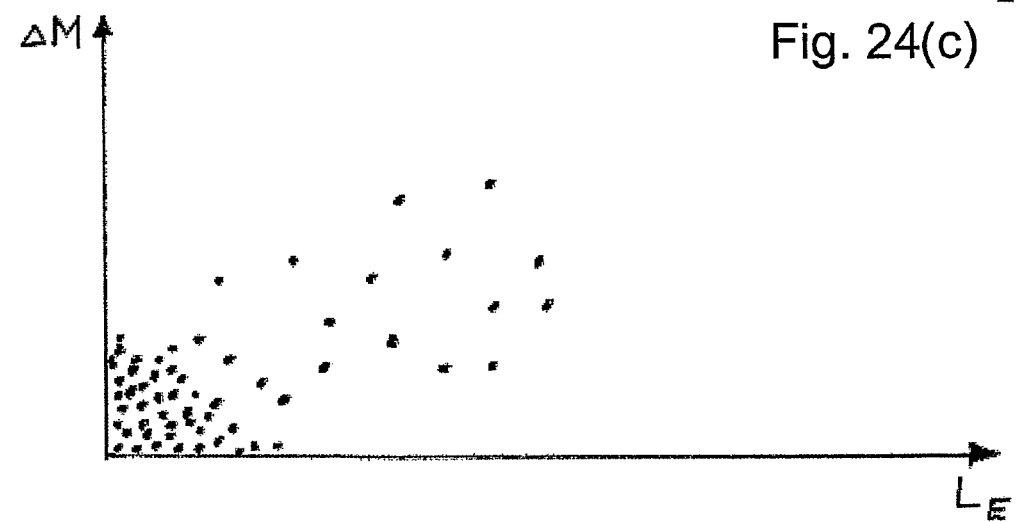

FIG. 24(b) shows a scatter diagram of the slubs on their own, as they are represented in FIG. 22(b). In particular, when the robust method for slub recognition described on the occasion of FIG. 21 is used, this scatter diagram will have no points which undesirably originate from imperfections such as thick places. Rather it only contains real slubs. FIG. 24(c) shows a scatter diagram of the virtual base yarn of FIG. 22(c). The points drawn therein do not represent slubs, but imperfections such as thick places. The scatter diagram of FIG. 24(c) may provide information on the applied yarn manufacturing process.

Other representation types such as e.g. the histograms of FIG. 5 may be used separately in an analogous manner for the data related on the one hand to the slub, and for the data related on the other hand to the virtual base yarn.

It may be advantageous in the method according to the invention to filter the readings as are represented somewhat in FIG. 2 or 4, according to certain filter criteria. Such filter criteria may for example be the following:

yarn imperfections such as neps, thick- and/or thin places. Thus for example, it is known from CH-678'173 A5 or from U.S. Pat. No. 5,537,811 A, to arrange possible yarn errors in a table in the manner of a coordinate system, for setting the clearing limit of an electronic yarn cleaner. The abscissa of the coordinate system represents the error mass and the ordinate represents the error length. An upper and a lower clearing limit are applied in this coordinate system. Neps and thick places above the upper clearing limit, and thin places below the lower clearing limit are automatically removed from the yarn. One may proceed in an analogous manner also with the method according to the invention by way of defining at least one "clearing limit". Thick or thin places within this limit are filtered out and only slubs outside this limit are evaluated further and/or represented graphically.

Slub characteristics. Thus e.g. slubs which fall short or exceed a certain slub length $L_E$, which fall short or exceed a certain slub total mass $M_E$, which have or do not have a certain slub shape (cf. FIG. 19) etc. may be filtered out. Only the remaining slubs which are not filtered out are evaluated further and/or graphically represented. It is also possible to provide several different filters, so that for example, with a first filter, only short slubs, and with a second filter, only long slubs are able to be evaluated and/or graphically represented.

The method according to the invention preferably permits an interactive input of certain parameters on the part of an operating person. Such parameters to be inputted may be filter parameters for the filters discussed above. The basics for the evaluation may also be inputted as parameters, thus e.g. a defined base yarn mass $M_S$.

In the method according to the invention, it may be advantageous to provide an interface for outputting data which has been obtained in the method. Such data may e.g. be the fancy yarn parameters discussed above, which are transferred to simulation software. From this, the simulation software may be a simulation of the examined yarn of a sheet formation woven or knitted from the yarn. Such a simulation based on evaluation data is comparatively quick and simple compared to a simulation based on measurement data.

Of course, the present invention is not limited to the embodiments discussed above. The man skilled in the art, with the knowledge of the invention, is capable of deriving further variants which also belong to the subject-matter of the present invention. Individual features of the method according to the invention, which are described above, in particular the evaluation algorithms for the individual fancy yarn parameters, may also be applied detached from the graphic representation according to the invention. Although the present description is concentrated on the example of the capacitive measurement of the yarn mass, the invention is not limited to this scanning principle. Indeed, other scanning principles—possibly with other measurement variables—may be applied with the method according to the invention, e.g. the optical measurement of the yarn diameter. Combinations of different scanning principles are also possible.

LIST OF REFERENCE NUMERALS 1 device
2 scanning unit
23 first data lead
3 evaluation unit
34 second data lead
4 output unit
5 input unit
9 fancy yarn
91, 91' base yarn
92, 92' slub
93, 94 slub flanks
95 slub roof
100 measurement curve
101 noise floor
102, 102' signal peak
103, 103', 103* slub beginning
104, 104* slub end
105 local maximum of a peak
106 thin place next to slub
111-115 classes of slubs, slub populations
111.1-113.1 part areas of the scatter diagram
121 local maximum which belongs to the base yarn
122 local maximum which belongs to the slubs
131 distribution in the spectrogram
132 maximum of the distribution 121
133 peak in the spectrogram
A area below the measurement curve
B color blue
H frequency of a reading
$I_M$ mass interval
L period length
$L_E$ slub length
$L_S$ slub distance
$L_E+L_S$ slub distance
M mass per length unit
$M_E$ slub total mass $M_M$ mean of the measured mass per length unit
$M_S$ base yarn mass per length unit
$M_T$ threshold value
R color red
x length coordinate
ΔM mass increase of a slub.

The invention claimed is:

1. A method for the characterization of fancy yarn, the method comprising the steps of:
scanning at least one characteristic of the fancy yarn along a longitudinal direction of the fancy yarn,
evaluating values of the at least one scanned characteristic, and
outputting at least one result of the evaluated values in a graphic representation, wherein the graphic representation is a bar chart having bars allocated to slubs on the fancy yarn, composed of at least two parts, wherein at least one of the length and area of a first part indicates a characteristic of a slub, and at least one of the length and area of a second part indicates a characteristic of an adjacent base yarn.

2. The method according to claim 1, wherein different classes of slubs are identified by way of the graphic representation.

3. The method according to claim 1, wherein the evaluating step comprises producing a measurement curve from the values, and computing an area below the measurement curve.

4. The method according to claim 3, further comprising computing an area between the measurement curve and at least one of a previously determined base yarn mass and a previously determined base yarn diameter.

5. The method according to claim 1, wherein the at least one scanned characteristic is at least one of a mass of the fancy yarn and a diameter of the fancy yarn.

6. The method according to claim 1, wherein the at least one result is selected from the group of fancy yarn parameters that includes a base yarn mass, a base yarn diameter, a slub distance, a mass increase of a slub, a slub diameter increase, a slub diameter, a slub length, a slub total mass, an average yarn number, a number of slubs per length unit, a pattern length, a sub-pattern length, a shape, and a color.

7. The method according to claim 6, wherein a running number is associated with each slub, and the running number is stored together with parameters of the associated slub.

8. The method according to claim 6, wherein the at least one result includes at least one of minima, maxima, arithmetic mean, and standard deviation of the at least one characteristic, and a number of slubs per yarn length.

9. The method according to claim 1, wherein the step of evaluating includes at least one of smoothing and idealization of the values.

10. The method according to claim 9, wherein the step of evaluating includes linking of at least one of the smoothed and idealized values with associated values that have not been smoothed and idealized.

11. The method according to claim 10, wherein the linking is at a least one of a difference formation and a quotient formation.

12. The method according to claim 9, wherein the at least one of smoothing and idealization includes an approximation by straight stretch sections, and slubs of the fancy yarn are approximated as trapezoids, triangles or rectangles.

13. The method according to claim 1, wherein the step of evaluating includes filtering the values.

14. The method according to claim 9, wherein an individual graphic representation for the at least one of smoothed and idealized values is outputted.

15. The method according to claim 1, wherein an individual graphic representation for data produced by the linking step is outputted.

16. The method according to claim 1, wherein the characteristic of the slub is the slub length and the characteristic of the adjacent base yarn is the slub distance.

17. The method according to claim 1, wherein the characteristic of the slub is the slub mass and the characteristic of the adjacent base yarn is the base yarn mass.

* * * * *